(12) United States Patent
Manthey et al.

(10) Patent No.: US 7,564,950 B2
(45) Date of Patent: Jul. 21, 2009

(54) MULTI-LEAF COLLIMATOR BASED FIELD SIZE CLIPPING FOR AUTOMATIC ADAPTATION TO ALLOWED IMAGE AREA

(75) Inventors: Dieter Manthey, Clayton, CA (US); Dave Pond, Novato, CA (US); Johannes Stahl, Walnut Creek, CA (US); Ricardo Ahumada, Martinez, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/357,610

(22) Filed: Feb. 17, 2006

(65) Prior Publication Data

US 2007/0195936 A1 Aug. 23, 2007

(51) Int. Cl.
*G21K 1/04* (2006.01)
*G01N 23/04* (2006.01)
(52) U.S. Cl. .......................... 378/150; 378/62; 378/151
(58) Field of Classification Search ............. 378/62–65, 378/150–153, 19, 98.8, 147, 148, 210; 600/427–429
See application file for complete search history.

(56) References Cited

U.S. PATENT DOCUMENTS

| | | | | |
|---|---|---|---|---|
| 5,471,516 A | * | 11/1995 | Nunan | 378/65 |
| 5,784,431 A | * | 7/1998 | Kalend et al. | 378/65 |
| 5,847,403 A | * | 12/1998 | Hughes et al. | 250/505.1 |
| 6,118,847 A | * | 9/2000 | Hernandez-Guerra et al. | 378/65 |
| 6,222,544 B1 | * | 4/2001 | Tarr et al. | 715/839 |
| 6,322,249 B1 | * | 11/2001 | Wofford et al. | 378/207 |
| 6,335,961 B1 | * | 1/2002 | Wofford et al. | 378/65 |
| 6,385,287 B1 | * | 5/2002 | Dorner | 378/65 |
| 6,429,578 B1 | * | 8/2002 | Danielsson et al. | 313/105 CM |
| 6,519,316 B1 | * | 2/2003 | Collins | 378/65 |
| 6,535,574 B1 | * | 3/2003 | Collins et al. | 378/65 |
| 6,760,402 B2 | * | 7/2004 | Ghelmansarai | 378/65 |
| 6,822,252 B2 | * | 11/2004 | Svatos et al. | 250/505.1 |
| 6,853,703 B2 | * | 2/2005 | Svatos et al. | 378/65 |
| 6,891,178 B2 | * | 5/2005 | Xing | 250/505.1 |
| 2004/0068182 A1 | * | 4/2004 | Misra | 600/427 |
| 2005/0013406 A1 | * | 1/2005 | Dyk et al. | 378/65 |
| 2007/0041500 A1 | * | 2/2007 | Olivera et al. | 378/65 |

FOREIGN PATENT DOCUMENTS

WO WO 2004047179 A1 * 6/2004

* cited by examiner

*Primary Examiner*—Edward J Glick
*Assistant Examiner*—Anastasia Midkiff

(57) ABSTRACT

A system and method for capturing a portal image using a linear accelerator having a multi-leaf collimator (MLC) and an imager allows the portal image field to be automatically clipped using the multi-leaf collimator so that the projection of the portal image field onto the imager falls within the allowed image area of the imager. In this manner, portal images may be obtained in instances where the projection of the portal image field onto the flat-panel imager is larger than an allowed image area of the imager, or where the projection of the portal image field onto the imager is not centered and would extend beyond the allowed image area, so that radiation sensitive electronics outside of the allowed image area are protected from undesirable exposure to radiation.

19 Claims, 9 Drawing Sheets

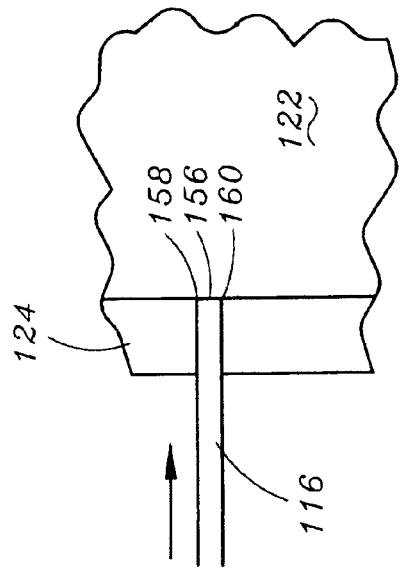
FIG. 7
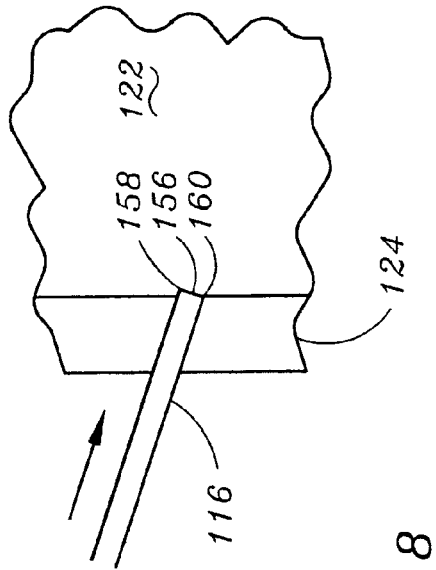
FIG. 8
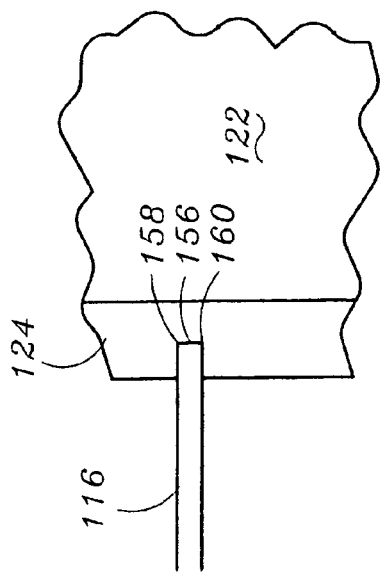
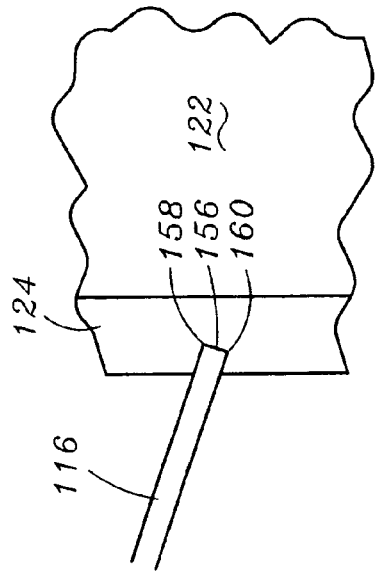

MULTI-LEAF COLLIMATOR BASED FIELD SIZE CLIPPING FOR AUTOMATIC ADAPTATION TO ALLOWED IMAGE AREA

BACKGROUND OF THE INVENTION

The present invention relates generally to the field of radiation therapy devices such as medical linear accelerators equipped with portal imaging systems, or the like, typically used for providing Image Guided Radiation Therapy (IGRT), and more particularly to a system and method for providing automatic field size clipping to the allowed image area of the imager of the portal imaging system using the multi-leaf collimator of the linear accelerator.

IGRT uses patient positioning devices and radiation imaging technologies such as portal imaging to target and treat cancerous tumors more precisely. Prior to the use of IGRT, radiation oncologists contended with variations in patient positioning, including variations caused by a patient's respiratory motion. Inevitably, a margin of healthy tissue around a treatment site was treated with radiation. However, the use of IGRT allows a radiation oncologist to determine the exact positioning of a treatment site before the administration of radiation.

Portal imaging used in IGRT employs a radiation therapy device such as a medical linear accelerator equipped with portal imaging system. The portal imaging system employs an imager such as an amorphous-silicon based flat-panel imager, or the like, to obtain images that may be used for treatment verification and patient positioning. Such flat-panel imagers include an active image area which is irradiated by the linear accelerator to generate the portal image. This active imaging area is typically surrounded by radiation sensitive electronics, which if exposed to radiation may be damaged or degraded. As a result, it is desirable that these electronics be protected from exposure to radiation.

To protect the sensitive electronics of the flat-panel imager, portal imaging systems typically prevent the user from acquiring an image if the projection of the planned portal image field onto the flat-panel imager is larger than an allowed image area of the imager which is equal to or less than the active image area, or if the projection of the portal image field is not centered and would extend beyond this allowed image area. This limitation greatly reduces the usability of the portal imaging system.

Consequently, it would be desirable to allow users of medical linear accelerators equipped with portal imaging systems to acquire portal images by automatically clipping the planned field size in instances where the projection of the portal image field onto the flat-panel imager is larger than an allowed image area of the imager, or where the projection of the image field is not centered and would extend beyond this allowed image area.

SUMMARY OF THE INVENTION

Accordingly, the present invention is directed to a system and method for capturing a portal image using a linear accelerator having a multi-leaf collimator and an imager having an allowed image area. The system and method utilize the multi-leaf collimator to automatically clip the portal image field so that the projection of the portal image field onto the imager falls within the allowed image area. In this manner, portal images may be obtained in instances where the planned portal image field size dictates an image area larger than the allowed image area of the imager, or where the portal image field is not centered and the resulting projection of the portal image field onto the imager would extend beyond the allowed image area.

In one exemplary embodiment, the present invention provides a system for capturing a portal image. The system includes a controller for receiving portal image field information, wherein the portal image field information includes a portal image field size defining an area of the portal image. The system further includes a linear accelerator for generating a beam of radiation. The linear accelerator includes a multi-leaf collimator having a plurality of leaves movable for selectively blocking at least a part of the beam of radiation for clipping the portal image field and an imager for capturing a portal image when irradiated by the beam of radiation. The controller calculates a leaf position for at least one leaf of the plurality of leaves of the multi-leaf collimator for clipping the portal image field to an allowed size corresponding to an area of the imager suitable for being irradiated by the beam of radiation.

In another exemplary embodiment, the present invention provides a method for capturing a portal image using a linear accelerator having a multi-leaf collimator and an imager. The method includes the steps of receiving portal image field information, the portal image field information including a portal image field size defining an area of the portal image; calculating a leaf position for at least one leaf of the multi-leaf collimator for clipping the portal image field to an allowed size corresponding to an area of the imager suitable for being irradiated; controlling the multi-leaf collimator to move the at least one leaf of the multi-leaf collimator to the calculated leaf position; and acquiring the portal image from the imager.

It is to be understood that both the foregoing general description and the following detailed description are exemplary and explanatory only and are not necessarily restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which:

FIG. 7 is a diagrammatic view illustrating the adjustment of an individual leaf of the multi-leaf collimator during clipping of the portal image field, wherein the portal image field is aligned to a major axis of the collimator;

FIG. 8 is a diagrammatic view illustrating the adjustment of an individual leaf of the multi-leaf collimator during clipping of the portal image field, wherein the portal image field is rotated with respect to a major axis of the collimator;

DETAILED DESCRIPTION OF SPECIFIC EMBODIMENTS

Reference will now be made in detail to the presently preferred embodiments of the invention, examples of which are illustrated in the accompanying drawings.

Referring generally to FIGS. 1 through 12, a system and method is described for capturing a portal image using a linear accelerator having a multi-leaf collimator and an imager, wherein the portal image field may be automatically clipped to account for the allowed image area of the imager using the multi-leaf collimator in accordance with an exemplary embodiment of the present invention. In this manner, the present invention provides for automatic optimization of a selected portal image field size to accommodate the dimensions of the imager. It will be appreciated that clipping of the portal image field in accordance with the present invention has no impact on the clinical usage of the linear accelerator since no clinical information is lost due to clipping of the portal image field. The projection of the clipped area falls outside of the imaging area of the imager is therefore not visible (i.e. not detectable by the imager).

Figure 1:
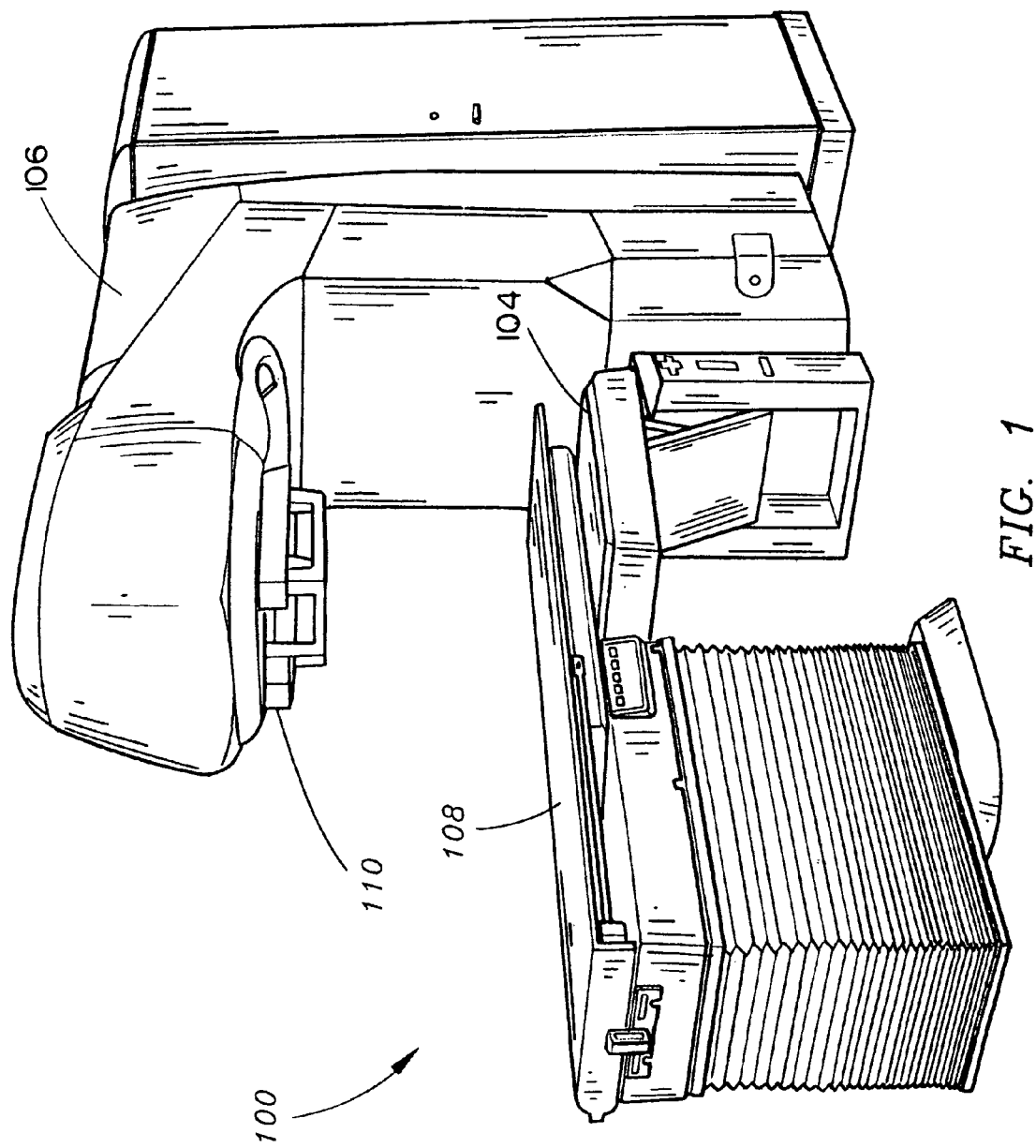
FIG. 1 is an isometric view illustrating an medical linear accelerator (LINAC) having a portal imaging system including a flat-panel imager for acquiring a portal image in accordance with an exemplary embodiment of the present invention.
Figure 2:
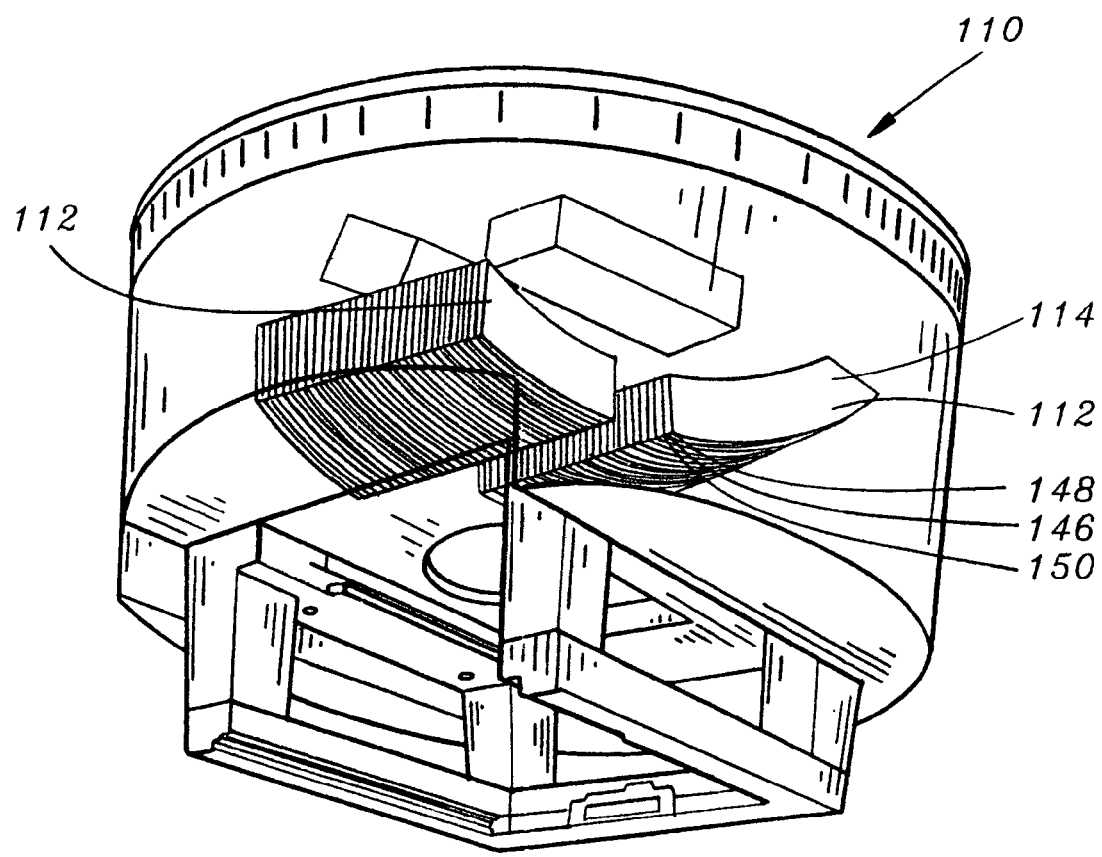
FIG. 2 is an isometric view illustrating the multi-leaf collimator of the medical linear accelerator shown in FIG. 1.

FIG. 1 illustrates an exemplary medical linear accelerator 100 used with a portal imaging system 102 (FIG. 5) according to the present invention. The portal imaging system 102 employs a flat-panel imager 104 such as an amorphous-silicon based flat-panel imager, or the like, to obtain portal images that may be used for treatment verification and patient positioning of patients undergoing radiation therapy. As shown in FIG. 1, the medical linear accelerator 100 includes a gantry 106 which is capable of rotating about a table or bed 108 on which the body of a patient undergoing radiation therapy is supported. The gantry 106 houses a radiation source such as a linear accelerator (LINAC), or the like, for generating a beam of high-energy radiation (e.g., X-ray or subatomic particle radiation having energies in the megavolt (MV) range) suitable for treatment of diseased tissue such as cancerous tumors, or the like, within the body of the patient. The gantry 106 further includes a multi-leaf collimator 110 which defines the size and shape of the beam of radiation delivered to the body by the LINAC. As shown in FIG. 2, the multi-leaf collimator 110 comprises a plurality of leaves 112 formed of a radiation absorbing material such as tungsten or lead, which can be moved independently of one another for shaping the beam of radiation. In the embodiment illustrated, the multi-leaf collimator 110 includes 82 individual leaves 112 arranged in 41 leaf pairs 114. In this embodiment, each leaf 112 is sized so that the projection 116 of the leaf 112 (FIGS. 7 and 8) in the isocentric plane of the linear accelerator 100 is 1 cm wide.

Figure 3:
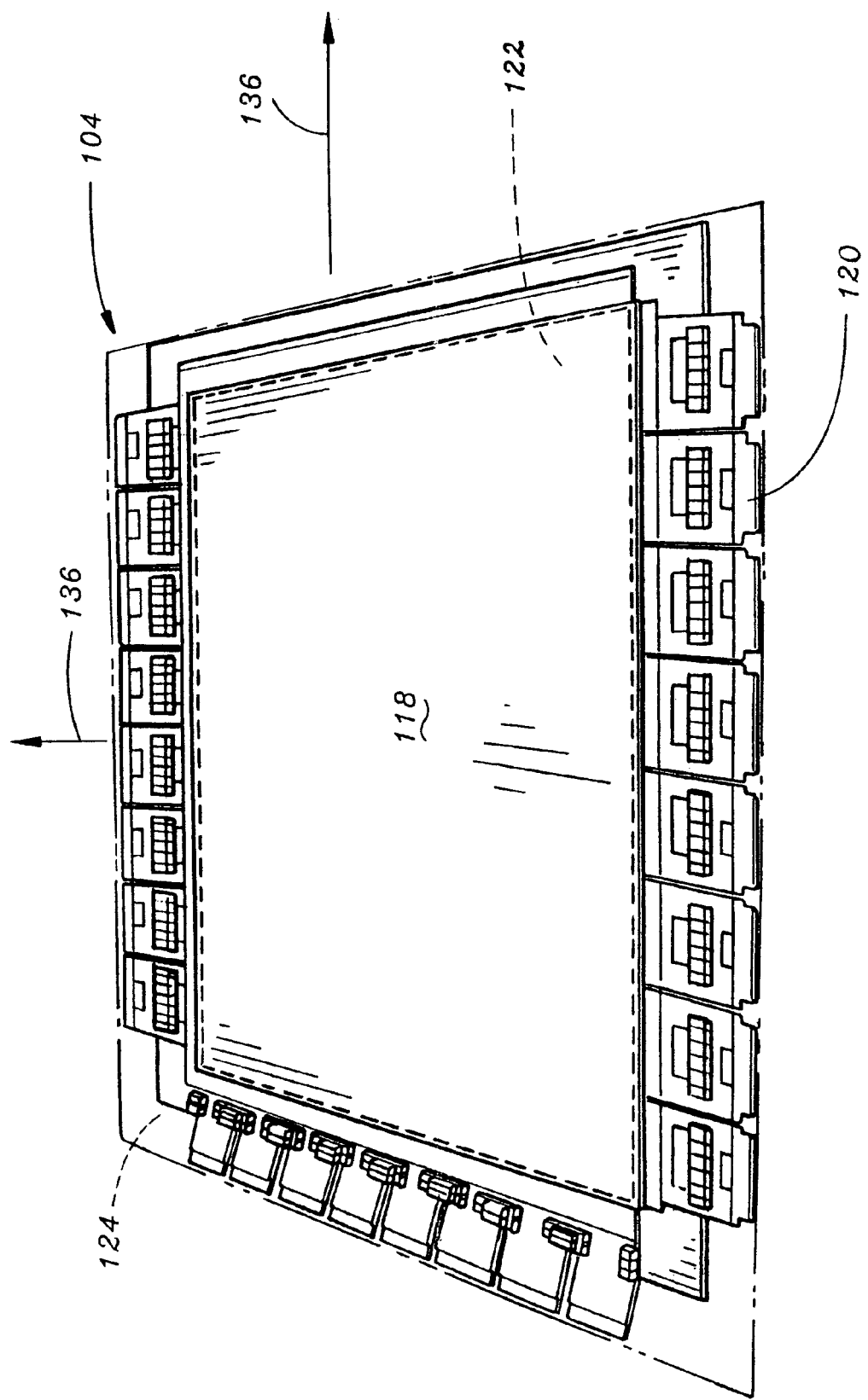
FIG. 3 is an isometric view illustrating the flat-panel imager of the medical linear accelerator shown in FIG. 1.

In the embodiment shown in FIG. 1, the flat-panel imager 104 is supported by the gantry 106 opposite the collimator 110. As shown in FIG. 3, the flat-panel imager 104 includes an active imaging area 118 which is irradiated by the beam of radiation from the LINAC for generating a portal image. This active imaging area 118 may be surrounded by radiation sensitive electronics 120, which if exposed to radiation may be damaged or degraded. As a result, it is desirable that these electronics 120 be protected from exposure to radiation. Thus, as shown in FIG. 3, the flat-panel imager 104 may be viewed as having an allowed image area 122 which does not contain components that may be degraded by exposure to radiation. The allowed image area 122 is surrounded by a protected area 124 corresponding to the areas of the imager 104 containing radiation sensitive electronics. In exemplary embodiments, the allowed image area 122 is equal to or smaller in size than the active imaging area 118.

Figure 4:
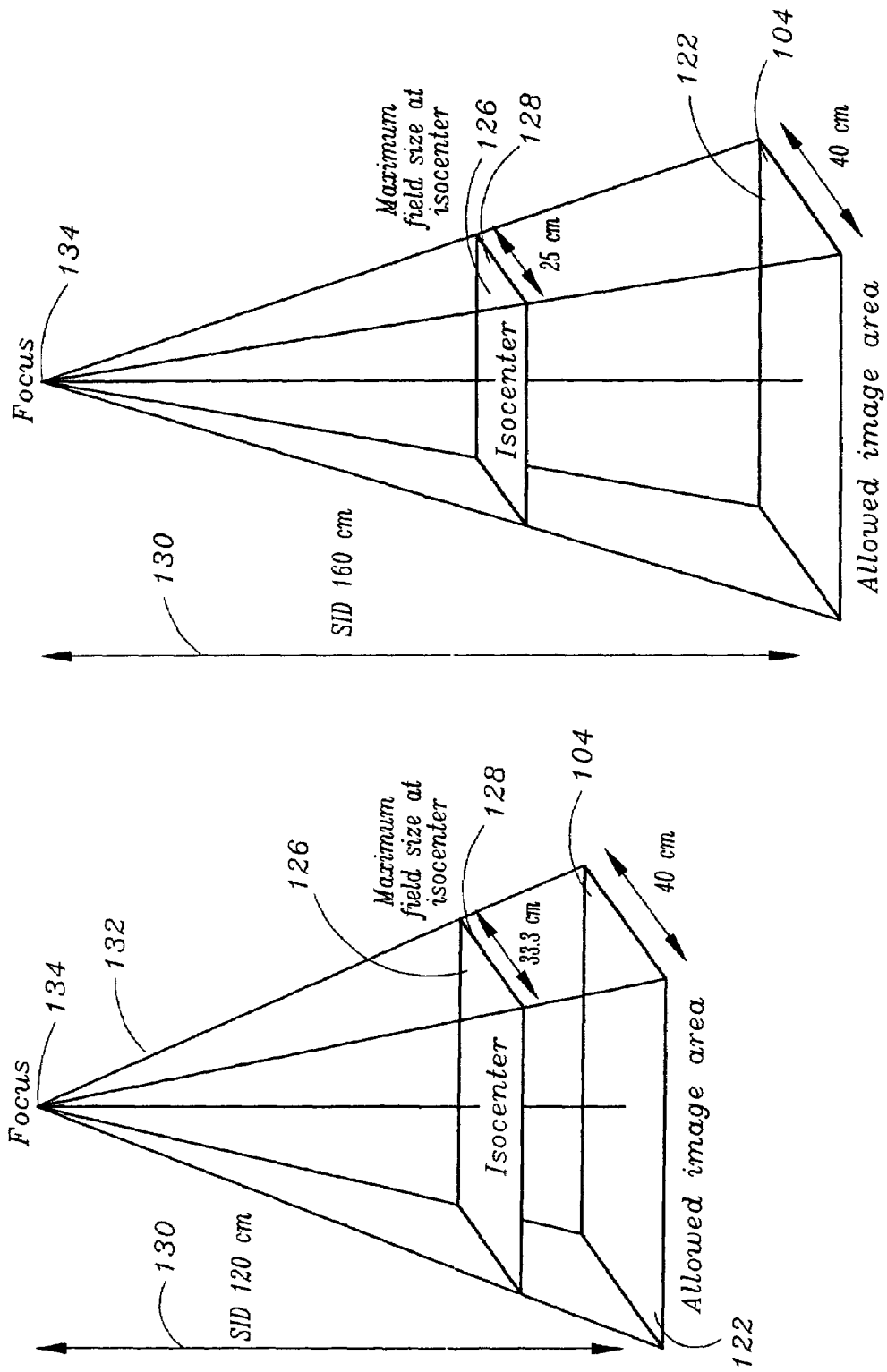
FIG. 4 is a diagrammatic view illustrating the relationship between the portal image field, the allowed image area of the flat-panel imager and the source to image distance (SID) of the portal imaging system of the medical linear accelerator shown in FIG. 1.

FIG. 4 illustrates the relationship between the maximum portal image field 128, the allowed image area 122 of the flat-panel imager 104 and the source to image distance (SID) of the portal imaging system 102 of the medical linear accelerator 100 shown in FIG. 1. The port or treatment field is the area of the body of the patient being treated through which the beam of radiation is directed to reach the diseased tissue of the body (e.g., a cancerous tumor). Treatment field size and portal image field size are defined in the isocentric plane 126 of the linear accelerator 100. The maximum field size of the portal image field 128 of a portal image is the maximum size, which, when projected onto the flat-panel imager 104, falls within the allowed image area 122 so that the beam of radiation producing the image does not irradiate the protected area 124 of the imager 104. Preferably, the flat-panel imager 104 can be deployed at a variable Source to Image Distance (SID). The SID is the distance 130 from the source of the beam of radiation 132 (e.g., the focus 134). In the exemplary portal imaging system 102 illustrated, the SID may be varied from approximately 115 cm to approximately 160 cm. However, it is contemplated that other SID ranges may be possible depending on the configuration of the medical linear accelerator employed. As the SID is increased, for example, by moving the flat-panel imager 104 away from the isocenter, the area of the maximum field size of the portal image field 128 is decreased. Conversely, as the SID is decreased, for example, by moving the flat-panel imager 104 toward the isocenter, the area of the maximum field size is increased. For example, a medical linear accelerator 100 having a SID that may be varied from 115 cm to 160 cm and a flat-panel imager 104 with an allowed image area 122 of 40×40 $cm^2$ has maximum field size of 33.3×33.3 $cm^2$ at a SID of 120 cm. This maximum field size decreases to 25×25 $cm^2$ as the SID increases to 160 cm. The maximum field size may further be reduced if the field is rotated or not centered with respect to a major axis 136 of the flat-panel imager 104, thereby further degrading the usability of the portal imaging system 102.

Figure 5:
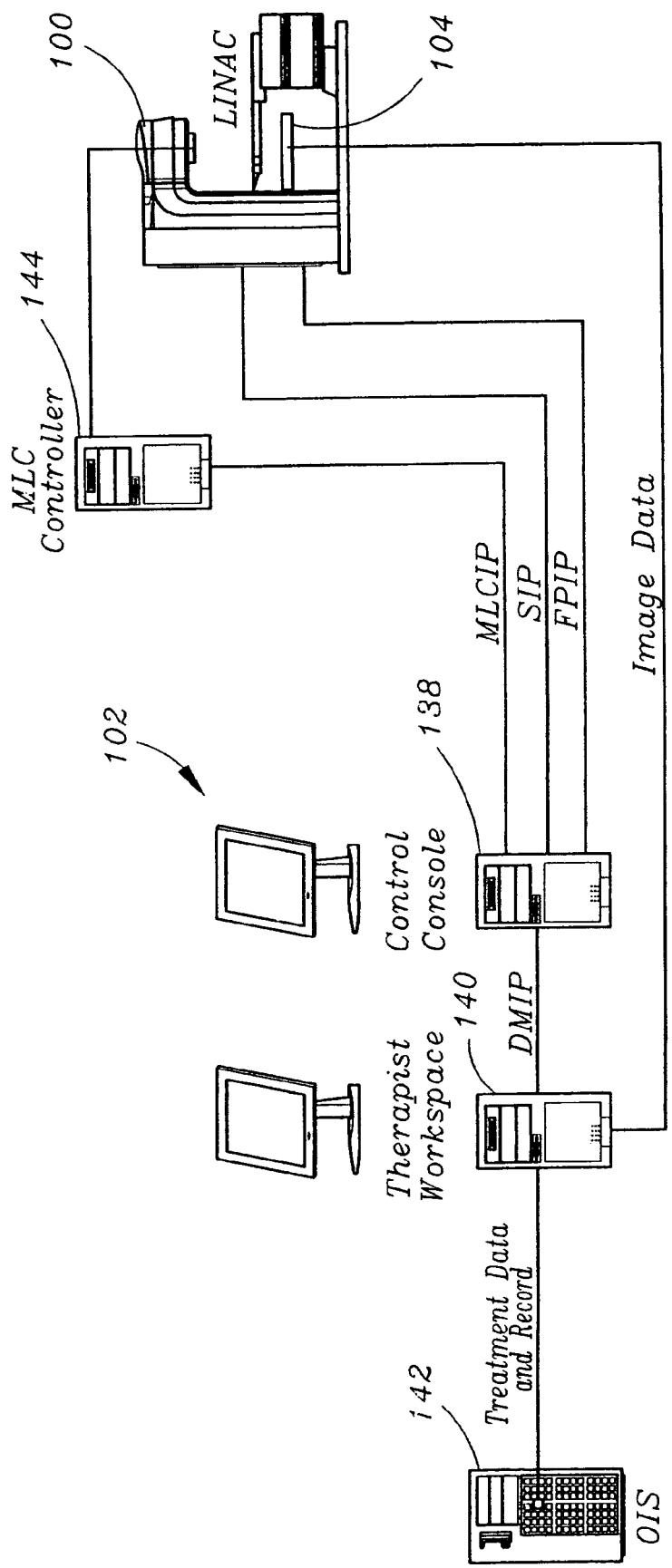
FIG. 5 is a block diagram illustrating a portal imaging system suitable for use with the medical linear accelerator shown in FIG. 1.

FIG. 5 illustrates a portal imaging system 102 suitable for use with the medical linear accelerator 100 shown in FIG. 1 for acquiring portal images in accordance with an exemplary embodiment of the present invention. As shown, the portal imaging system 102 includes a controller, such as the control console 138 of the linear accelerator 100, and a therapist workspace 140. The therapist workspace 140 is coupled to an Oncology Information System (OIS) 142 via a network connection, or the like. In exemplary embodiments, the OIS 142 includes a database that stores treatment plans containing information used by doctors, oncology therapists, and the like for managing the treatment of patients undergoing radiation therapy.

In exemplary embodiments, the therapist workspace 140 comprises a computer, or the like, which provides access to the OIS 142. Using the therapist workspace 140, a user such as an oncology therapist, technician, or the like, may retrieve and read a treatment plan from the OIS 142 for a patient undergoing radiation therapy. The treatment plan, which includes treatment data for the patient, is used to develop treatment parameters for controlling the provision of radiation therapy to the patient via the linear accelerator 100. Where a portal image is to be acquired, the treatment parameters may include portal imaging settings for the portal imaging system 102. The portal imaging settings may include portal image field information defining the position, size and shape of the portal image field with respect to the isocentric plane of the linear accelerator 100 and the body of the patient undergoing treatment. The therapist workspace 140 downloads the portal image field information to the control console 138 using a suitable interface protocol, such as the Digital MEVATRON Interface Protocol (DMIP) developed by Siemens Medical Solutions USA, Inc., or the like.

In exemplary embodiments, the portal image field information includes a planned portal image field size defining the area of the desired portal image to be acquired by the portal imaging system 102. Typically, the planned portal image field size is independent of the maximum allowed image area 122 of the flat-panel imager 104. Thus, the planned portal image field may extend beyond the allowed image area 122 into the protected area 124 or beyond. The control console 138, which, like the therapist workspace 140, comprises a computer, or the like, compares the planned portal image field size with the maximum allowed image area 122 of the flat panel imager 104. If the projection of any portion of the planned portal image field 128 is determined to extend beyond that the maximum allowed image area 122 (e.g., the projection of the planned portal image field 128 is greater than the allowed image area 122 or the planned portal image field 128 is rotated with respect to the allowed image area 122 so that a portion of the projection of the planned portal image field 128 is outside of the allowed image area 122), the control console 138 asserts an interlock which inhibits operation of the linear accelerator 100 to prevent irradiation of the flat-panel imager 104. If the planned portal image field 128 retrieved from the treatment plan requires clipping, the control console 138 programs the portal image field calculates leaf positions for one or more of the leaves 112 of the multi-leaf collimator 110 without clipping and informs the user that the planned portal image field is not acceptable (e.g., by displaying an interlock message to the user) allowing the user to choose to have the portal image field 128 clipped. If the user chooses to have the portal image field 128 clipped, the control consol 138 initiates clipping and de-asserts or clears the interlock. In multiple segmented treatment plans where multiple portal image fields are to be programmed sequentially, subsequent portal image fields retrieved from the treatment plan after the initial interlock is cleared are clipped before the fields are programmed and no additional interlock is asserted.

The control console 128 automatically adapts or clips the portal image field 128 to the allowed image area 122 by calculating leaf positions for one or more of the leaves 112 of the multi-leaf collimator 110. The control console 138 then downloads the resulting positions of the leaves 112 of the multi-leaf collimator 110 to the multi-leaf collimator (MLC) controller 144 using a suitable interface protocol such as the Multi-leaf Collimator Interface Protocol (MLCIP) developed by Siemens Medical Solutions USA, Inc., or the like. The MLC controller 144 commands the multi-leaf collimator 110 to move one or more leaves 112 as necessary to place the leaves 112 in the leaf positions calculated by the control console 138, thereby positioning the leaves 112 in position to clip or shape the beam of radiation emitted by the LINAC so that the portal image field is clipped so that its projection falls with the allowed image area 122 of the flat-panel imager 104.

During clipping, the control console 138 continues to compare the portal image field size, as clipped at that point in the clipping process, with the maximum allowed image area 122 of the flat panel imager 104. While any portion of the projection of the portal image field 128 is determined to extend beyond that the maximum allowed image area 122 (e.g., the projection of the portal image field 128 is greater than the allowed image area 122 or the portal image field 128 is rotated with respect to the allowed image area 122 so that a portion of the portal image field 128 is outside of the allowed image area 122), the control console 138 continues to assert the interlock so that the flat-panel imager 104 is not irradiated. When the control console 138 determines that the projection of the clipped portal image field 128 is entirely within the allowed image area 122, the interlock is deasserted allowing operation of the linear accelerator 100 and irradiation of the flat-panel imager 104 for capturing a portal image. Preferably, the interlock function provided by the control console 138 is independent of the portal image clipping process, thereby functioning as a fail-safe for preventing exposure of the flat-panel imager 104 to radiation should clipping of the portal image field be unsuccessful (e.g., due to mechanical failure, or the like).

As shown in FIG. 5, the control console 138 may further calculate parameters for controlling operation of the LINAC, and for positioning the gantry 106 and the patient table 108 of the linear accelerator 100. The control console 138 uses these parameters to generate commands which may then be downloaded to the linear accelerator 100 via a Serial Interface Protocol (SIP), or like protocol, for controlling operation of the linear accelerator 100. Similarly, the control console 138 may generate commands for controlling the positioning and operation of the flat-panel imager 104. As shown, these commands are transmitted to the flat-panel imager 104 via a suitable interface protocol, such as the Flat Panel Interface Protocol (FPIP) developed by Siemens Medical Solutions USA, Inc., or the like. The flat-panel imager 104 transmits portal image data to the therapist workspace 140, which uses the data to generate a portal image to be displayed to the user.

Figure 6:
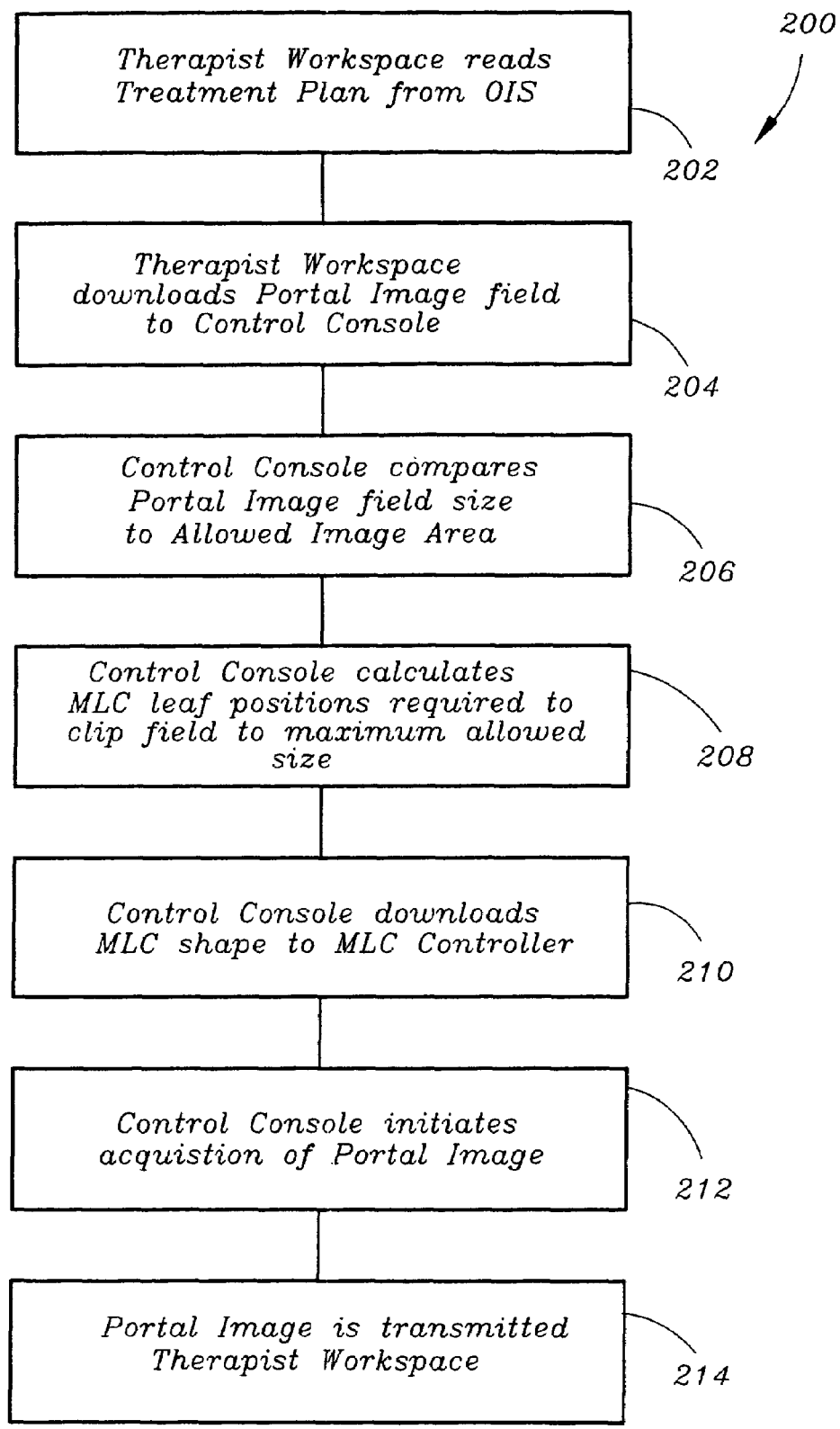
FIG. 6 is a flow diagram illustrating a method for acquiring a portal image using the portal imaging system shown in FIG. 7, wherein the portal image field may be automatically clipped to account for the allowed image area of the imager using the multi-leaf collimator of the medical linear accelerator.

FIG. 6 illustrates an exemplary method 200 for acquiring a portal image using the portal imaging system 102 shown in FIG. 4. First, portal image field information including a planned portal image field size defining an area for the portal image is retrieved for acquiring the portal image. For example, in step 202, a user such as an oncology therapist, technician, or the like, retrieves and reads a treatment plan including portal imaging settings having portal image field information from the OIS 142 for a patient undergoing radiation therapy via the therapist workspace 140, as described in the discussion of FIG. 5. The portal image field information is then downloaded to the control console 138 using a suitable interface protocol, such as the Digital Mevatron Interface Protocol (DMIP) developed by Siemens Medical Solutions USA, Inc., or the like, in step 204. Next, the control console 138 determines the planned portal image field size from the portal image field information and compares the planned portal image field size with the maximum allowed image area 122 of the flat panel imager 104, at step 206. Leaf positions are calculated for the leaves 112 of the multi-leaf collimator 110 for generating an MLC shape which clips the planned portal image field to an allowed size corresponding to allowed image area 122 of the flat-panel imager 104, at step 208. The calculated MLC shape is then downloaded to the MLC controller 144, at step 210, which causes the multi-leaf collimator 110 to move the leaves 112 to the calculated leaf positions. The control console 138 then initiates acquisition of the portal image at step 212, which is transmitted to the therapist workspace 140, at step 214, and displayed to the user.

FIGS. 7 and 8 illustrate the adjustment of an individual leaf 112 of the multi-leaf collimator 110 shown in FIG. 2 during clipping of the portal image field to the allowed image area 122 of the flat-panel imager 104. FIG. 7 illustrates clipping of the portal image field when the portal image field is aligned to a major axis 136 of flat-panel imager 104 (FIG. 3), while FIG. 8 illustrates clipping of the portal image field where the portal image field is rotated with respect to a major axis 136 (e.g., the multi-leaf collimator 110 is rotated with respect to the flat-panel imager 104).

Viewed from above, each leaf 112 of the multi-leaf collimator 110 shown in FIG. 2 includes a frontal edge 146 having a first (e.g., left) corner 148 and a second (e.g., right) corner 150. A planned leaf position is determined for positioning the leaf 112 to provide (in combination with the other leaves 112 of the collimator 110) a collimator radiation aperture suitable for shaping the beam of radiation so that the beam radiates a field in the isocentric plane of the linear accelerator 100 having the planned portal image field size. When moved to the planned leaf position, the leaf 112 casts a projection or shadow 156 onto the flat-panel imager 104 which includes projections 158 & 160 of the first and second corners 148 & 150 of the frontal edge 146 of the leaf 112. In accordance with the present invention, the position of the projections 158 & 160 of the first and second corners 148 & 150 onto the flat-panel imager 104 are determined. If both the projection 158 of the first corner 148 and the projection 160 of the second corner 150 fall within the allowed image area 122, the leaf position is not changed. However, if either the projection 158 of the first corner 148 or the projection 160 of the second corner 150 fall outside of the allowed image area 122 (e.g., the projections 158 & 160 fall within the protected area 124, or beyond), a new leaf position is calculated for the leaf 112, wherein the projections 158 & 160 of both corners 148 & 150 are within the allowed image area 122. This calculation is repeated for each leaf of the multi-leaf collimator 110 thereby defining the shape of the collimator radiation aperture (MLC shape). If a position for a leaf 112 cannot be calculated so that the projections 158 & 160 of both corners 148 & 150 are within the allowed image area 122, the leaf 112 is moved inward until it abuts the opposing leaf 112 of the leaf pair 114. The MLC shape is then transmitted to the MLC controller 144, which causes each leaf 112 of the multi-leaf collimator 110 to be moved to the calculated position.

Figure 9:
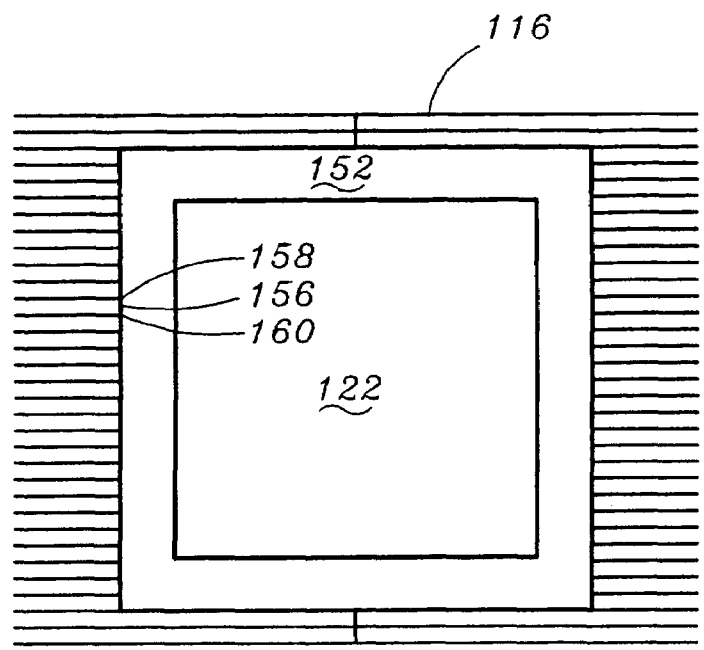
FIGS. 9 and 10 are diagrammatic views illustrating clipping of the planned portal image field to a clipped portal image field corresponding in size to the allowed image area using the multi-leaf collimator shown in FIG. 2, wherein the portal image field is aligned to a major axis of the flat-panel imager shown in FIG. 3.
Figure 10:
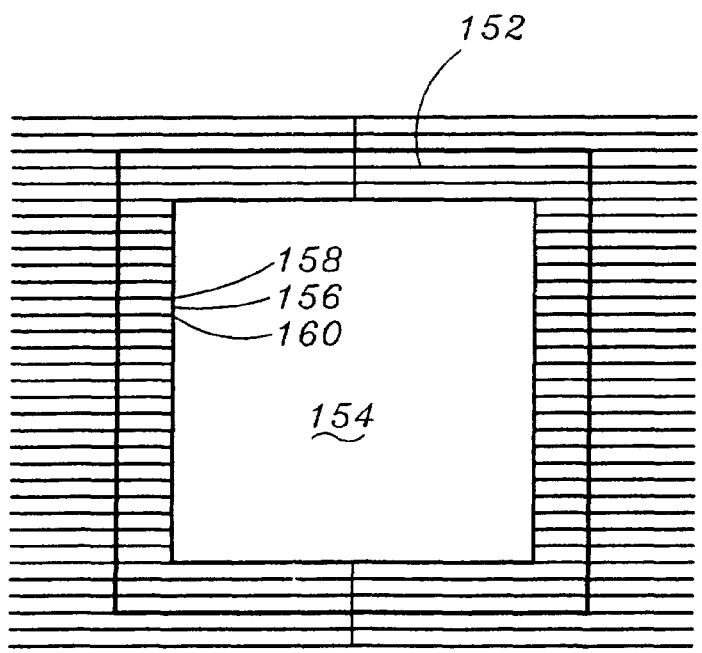
Figure 11:
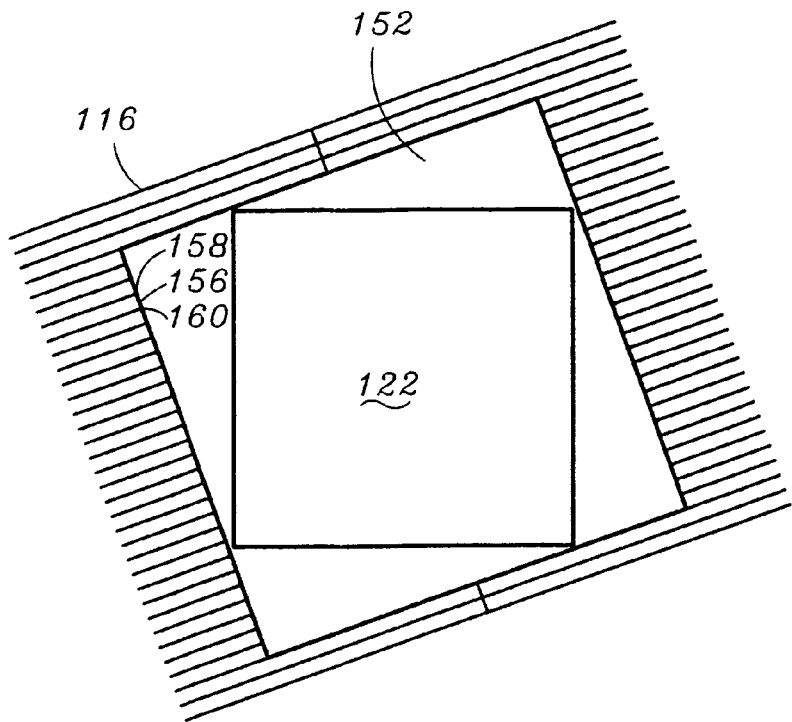
FIGS. 11 and 12 are diagrammatic views illustrating clipping of the planned portal image field to a clipped portal image field corresponding in size to the allowed image area using the multi-leaf collimator shown in FIG. 2, wherein the portal image field is rotated with respect to a major axis of the flat-panel imager shown in FIG. 3.
Figure 12:
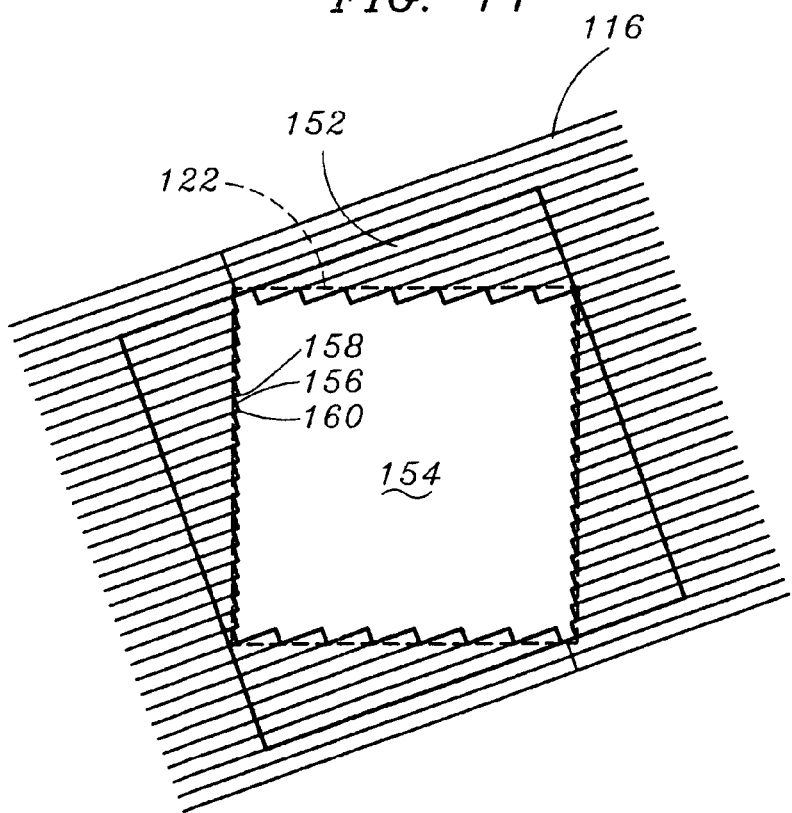

FIGS. 9 through 12 illustrate clipping of the planned portal image field 152 to provide a clipped portal image field 154 corresponding to the allowed image area 122 (FIG. 3) using the multi-leaf collimator 104 shown in FIG. 2. In FIGS. 9 and 10, the planned portal image field 152 is aligned to a major axis 136 of the flat-panel imager 104 (FIG. 3). In FIGS. 11 and 12, the planned portal image field 152 is rotated with respect to a major axis 136 (e.g., the multi-leaf collimator 110 is rotated with respect to the flat-panel imager 104). The planned portal image field 152 comprises the area within the projections 116 of the leaves 112 of the multi-leaf collimator 110 (FIG. 2). In the example shown, the planned portal image 152 extends beyond the allowed image area 122 of the flat-panel imager 104. Thus, one or both of the projection 158 of the first corner 148 and the projection 160 of the second corner 150 falls outside of the allowed image area 122 (e.g., fall within the protected area 124, or beyond). As shown in FIGS. 10 and 12, after clipping, the projections 158 & 160 of both corners 148 & 150 fall within the allowed image area 122 thereby defining the clipped portal image field 154 so that the clipped portal image field 154 is within the allowed image area 122 of the flat-panel imager 104.

FIGS. 1 through 12, illustrate an exemplary medical linear accelerator 100 having a portal imaging system 102 providing clipping of the portal image field of a portal image so that the projection of the portal image field onto the flat-panel imager 104 falls within the allowed image area 122 of the imager 104. However, it will be appreciated by those of skill in the art that the present invention is not necessarily limited to the specific portal imaging system 102 illustrated, but instead may be implemented in portal imaging systems 102 having a variety of software and/or hardware architectures. For example, in the embodiments illustrated, positions of the leaves 112 of the multi-leaf collimator are calculated by the control console 138 and transmitted to the MLC controller 144 which controls the multi-leaf collimator 110 to move the leaves 112 to the calculated positions. However, it is contemplated that calculation of leaf positions may be accomplished by other computing devices within the portal imaging system 102 (e.g., the therapist workspace 140, the MLC controller, a separate controller, or the like). In exemplary embodiments, the methods disclosed may be implemented as sets of instructions such as software or firmware readable by the control console 138 or like controller. It is understood that the specific order or hierarchies of steps in the methods disclosed are examples of exemplary approaches. Based upon design preferences, it is understood that the specific order or hierarchy of steps in the method can be rearranged while remaining within the scope of the present invention. The attached method claims present elements of the various steps in a sample order, and are not meant to be limited to the specific order or hierarchy presented.

For purposes of illustration, the medical linear accelerator 100 is shown in FIGS. 1 through 12 as employing a single MV radiation source and flat-panel imager 104 which are used by the portal imaging system 102 for generating portal images in accordance with the present invention. However, it is contemplated the linear accelerator 100 need not be limited to the specific configuration shown and instead may be modified as required by specific applications without departing from the scope and intent of the present invention. For example, in specific embodiments of the invention, the linear accelerator 100 may be configured for providing kV imaging in addition to MV portal imaging. In such embodiments, the linear accelerator 100 may be provided with a second radiation source such as a diagnostic X-ray tube for generating a beam if radiation having energies in the kilovolt (kV) range, mounted to gantry 106 or, alternatively, a second gantry (not shown), and a second imager configured for receiving the beam of radiation from the second radiation source for producing diagnostic images of the body of a patient undergoing radiation therapy.

It is believed that the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A method for capturing a portal image using a linear accelerator having a multi-leaf collimator and an imager, comprising:
   positioning the imager;
   receiving portal image field information, the portal image field information including a planned portal image field size for defining a portal image field;
   comparing the portal image field to an allowed image area of the imager that is suitable for being irradiated to determine if a maximum size of the portal image field exceeds the allowed image area of the imager, wherein the maximum size of the portal image field is inversely proportional to a distance between a radiation source of the linear accelerator and the imager;
   calculating a leaf position for at least one leaf of the multi-leaf collimator for clipping the portal image field, wherein the clipped portal image filed does not include a portion of the maximum size of the portal image field that exceeds the allowed image area of the imager so that a projection of the portal image field onto the imager falls within the allowed image area of the imager, wherein the clipped portal image field prevents irradiation of radiation-sensitive electronics of the imager;
   controlling the multi-leaf collimator to move the at least one leaf of the multi-leaf collimator to the calculated leaf position; and
   acquiring the portal image from the imager, wherein the at least one leaf comprises a frontal edge having a first corner and a second corner and calculating a leaf position for at least one leaf of the multi-leaf collimator comprises determining whether a projection of the first corner and a projection of the second corner onto the imager are within the allowed image area.

2. The method as claimed in claim 1, further comprising moving the leaf if either the projection of the first corner and the projection of the second corner are not within the allowed image area so that both the projection of the first corner and the projection of the second corner are within the allowed image area.

3. The method as claimed in claim 1, further comprising retrieving a treatment plan, the treatment plan including the portal image field information.

4. The method as claimed in claim 3, wherein the treatment plan is retrieved from an oncology information system (OIS).

5. The method as claimed in claim 1, further comprising ascertaining the planned portal image field size from the portal image field information.

6. The method as claimed in claim 1, further comprising providing the acquired portal image to a user.

7. A system for capturing a portal image, comprising:
   a controller for receiving portal image field information, the portal image field information including a planned portal image field size defining a portal image field;
   a linear accelerator for generating a beam of radiation, the linear accelerator including a multi-leaf collimator having a plurality of leaves movable for selectively blocking at least a part of the beam of radiation for clipping the portal image field; and
   an imager for capturing a portal image when irradiated by the beam of radiation, said imager including an allowed image area surrounded by radiation-sensitive electronics,
   wherein the controller positions the imager, compares the portal image field to the allowed image area to determine if a maximum size of the portal image field exceeds the allowed image area of the imager wherein the maximum size of the portal image field is inversely proportional to a distance between a source of the beam of radiation and the imager, and calculates a leaf position for at least one leaf of the plurality of leaves of the multi-leaf collimator for clipping the portal image field, acquiring the portal image from the imager, wherein the at least one leaf comprises a frontal edge having a first corner and a second corner, wherein calculating the leaf position comprises determining whether a projection of the first corner and a projection of the second corner onto the imager are within the allowed image area, and
   wherein the clipped portal image field does not include a portion of the maximum size of the portal image field that exceeds the allowed image area of the imager so that a projection of the portal image field onto the imager falls within said allowed image area of the imager that is suitable for being irradiated by the beam of radiation and prevents irradiation of the radiation-sensitive electronics of the imager.

8. The system as chimed in claim 7, further comprising a multi-leaf collimator controller for controlling the multi-leaf collimator to move the at least one leaf to the calculated leaf position.

9. The system as claimed in claim 8, wherein the at least one leaf comprises a frontal edge having a first corner and a second corner and calculating a leaf position for at least one leaf of the multi-leaf collimator comprises determining whether a projection of the first corner and a projection of the second corner onto the imager are within the allowed image area.

10. The system as claimed in claim 9, wherein the multi-leaf collimator controller causes the leaf to be moved if either the projection of the first corner and the projection of the second corner are not within the allowed image area so that both the projection of the first corner and the projection of the second corner are within the allowed image area.

11. The system as claimed in claim 10, wherein the leaf position is provided to the multi-leaf collimator controller via Multi-leaf Collimator Interface Protocol (MLCIP).

12. The system as claimed in claim 7, further comprising a therapist workspace for retrieving a treatment plan, the treatment plan including the image field information, and providing the image field information to the controller.

13. The system as claimed in claim 12, wherein the treatment plan is retrieved from an oncology information system (OIS).

14. The system as claimed in claim 12, wherein the therapist workspace provides the portal image to a user.

15. The system as claimed in claim 7, wherein the controller ascertains the portal image field size from the portal image field information.

16. The system as claimed in claim 7, wherein the imager comprises an amorphous-silicon flat-panel imager.

17. The system as claimed in claim 16, wherein the controller positions the imager via Flat Panel Interface Protocol (FPIP).

18. The system as claimed in claim 7, wherein the controller compares the projection of the portal image field with the allowed image area of the imager and asserts an interlock for preventing radiation of the imager if the projection of the portal image field is determined to extend outside of the allowed image area.

19. A system for capturing a portal image, comprising:
   means for positioning an imager;
   means for receiving portal image field information, the portal image field information including a portal image field size for defining a portal image field;

means for comparing the portal image filed to an allowed image area of the imager that is suitable for being irradiated to determine if a maximum size of the portal image field exceeds the allowed image area of the imager, wherein the maximum size of the portal image field is inversely proportional to a distance between a radiation source and the imager;

means for calculating a leaf position for at least one leaf of a multi-leaf collimator for clipping the portal image field, wherein the at least one leaf comprises a frontal edge having a first corner and a second corner, wherein calculating the leaf position comprises determining whether a projection of the first corner and a projection of the second corner onto the imager are within the allowed image area, and wherein the clipped portal image field does not include a portion of the maximum size of the portal image field that exceeds the allowed image area of the imager so that the projection of the portal image field onto the imager falls within an allowed image area of the imager and prevents irradiation of radiation-sensitive electronics surrounding the allowed image area of the imager;

means for controlling the multi-leaf collimator to move the at least one leaf of the multi-leaf collimator to the calculated leaf position; and means for acquiring the portal image.

\* \* \* \* \*